US011253485B2

(12) United States Patent
Dodge et al.

(10) Patent No.: US 11,253,485 B2
(45) Date of Patent: Feb. 22, 2022

(54) SLOW INTRAVENTRICULAR DELIVERY

(71) Applicant: Genzyme Corporation, Cambridge, MA (US)

(72) Inventors: James C. Dodge, Bridgewater, NJ (US); Marco A. Passini, Northborough, MA (US); Lamya S. Shihabuddin, Bridgewater, NJ (US); Seng H. Cheng, Natick, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 16/281,961

(22) Filed: Feb. 21, 2019

(65) Prior Publication Data
US 2019/0328682 A1 Oct. 31, 2019

Related U.S. Application Data

(63) Continuation of application No. 12/187,896, filed on Aug. 7, 2008, now abandoned, which is a continuation of application No. PCT/US2007/003382, filed on Feb. 8, 2007.

(60) Provisional application No. 60/771,451, filed on Feb. 9, 2006.

(51) Int. Cl.
*A61K 31/00* (2006.01)
*A61K 9/00* (2006.01)

(52) U.S. Cl.
CPC ............ *A61K 31/00* (2013.01); *A61K 9/0024* (2013.01)

(58) Field of Classification Search
CPC ....... A61K 31/00; A61K 9/0024; A61P 11/00; A61P 13/12; A61P 1/16; A61P 23/00; A61P 25/00; A61P 25/08; A61P 25/14; A61P 25/16; A61P 25/28; A61P 3/00; A61P 3/08; A61P 3/10; A61P 43/00
See application file for complete search history.

(56) References Cited

U.S. PATENT DOCUMENTS

| | | | |
|---|---|---|---|
| 5,670,488 A | 9/1997 | Gregory et al. | |
| 5,720,720 A | 2/1998 | Laske et al. | |
| 5,814,014 A | 9/1998 | Elsberry et al. | |
| 5,882,877 A | 3/1999 | Gregory et al. | |
| 5,994,136 A | 11/1999 | Naldini et al. | |
| 6,013,516 A | 1/2000 | Verma et al. | |
| 6,042,579 A | 3/2000 | Elsberry et al. | |
| 6,689,756 B2 | 2/2004 | Hesson et al. | |
| 8,926,967 B2 | 1/2015 | Dodge et al. | |
| 10,080,783 B2 | 9/2018 | Dodge et al. | |
| 2002/0130079 A1 | 12/2002 | Saxton et al. | |
| 2002/0183683 A1 | 12/2002 | Lerner | |
| 2003/0022879 A1 | 1/2003 | Hesson et al. | |
| 2003/0163181 A1 | 8/2003 | Frazer et al. | |
| 2004/0105888 A1 | 5/2004 | Pratt | |
| 2004/0258666 A1 | 12/2004 | Passini et al. | |
| 2005/0026823 A1 | 2/2005 | Zankel et al. | |
| 2005/0048047 A1 | 5/2005 | Kakkis | |
| 2005/0102708 A1 | 5/2005 | Lecanu et al. | |
| 2005/0208090 A1 | 9/2005 | Keimeal et al. | |
| 2009/0105141 A1 | 4/2009 | Dodge | |
| 2009/0123451 A1 | 5/2009 | Dodge et al. | |
| 2009/0130079 A1 | 5/2009 | Dodge et al. | |
| 2010/0173979 A1 | 7/2010 | Dodge et al. | |
| 2015/0313970 A1 | 11/2015 | Dodge et al. | |
| 2019/0083582 A1 | 3/2019 | Dodge et al. | |
| 2021/0228692 A1 | 7/2021 | Dodge et al. | |

FOREIGN PATENT DOCUMENTS

| | | |
|---|---|---|
| EP | 0130166 A1 | 12/1991 |
| JP | 2009-525963 A | 7/2009 |
| RU | 2179034 C2 | 2/2002 |
| WO | WO-95/29993 A1 | 11/1995 |
| WO | WO-96/33280 A1 | 10/1996 |
| WO | WO-96/40955 A1 | 12/1996 |
| WO | WO-97/00326 A1 | 1/1997 |
| WO | WO-97/25446 A1 | 7/1997 |
| WO | WO-98/11206 A2 | 3/1998 |
| WO | WO-99/57296 A1 | 11/1999 |
| WO | WO-2005/002515 A1 | 1/2005 |
| WO | WO-2005/002515 A2 | 1/2005 |
| WO | WO-2005/002515 A3 | 1/2005 |
| WO | WO-2005/021064 A2 | 3/2005 |
| WO | WO-2005/021064 A3 | 3/2005 |
| WO | WO-2005/072049 A2 | 8/2005 |
| WO | WO-2005/095955 A1 | 10/2005 |
| WO | WO-2007/084737 A2 | 7/2007 |
| WO | WO-2007/084737 A3 | 7/2007 |
| WO | WO-2007/095056 A2 | 8/2007 |
| WO | WO-2007/095056 A3 | 8/2007 |

OTHER PUBLICATIONS

Abruzzese, R.V. et al. (Jun. 10, 1999). "Ligand-Dependent Regulation of Plasmid-Based Transgene Expression in Vivo," *Hum. Gene Ther.* 10(9):1499-1507.
Belichenko, P.V. et al. (Jul. 11, 2005). "Penetration, Diffusion, and Uptake of Recombinant Human α-L-Iduronidase after Intraventricular Injection Into the Rat Brain," *Molecular Genetics and Metabolism* 86(1-2):141-149.
Bembi, et al. (Sep. 1995). "Cerebrospinal Fluid infusion of Alglucerase in the Treatment of Acute Neuronopathic Gaucher's Disease," *Pediatric Research* 38(3):425(Abstract#14). Berkner, K.L. (1992). "Expression of Heterologous Sequences in Adenoviral Vectors," *Curr. Top Micro, and Immunol.* 158:39-66.

(Continued)

*Primary Examiner* — Blaine Lankford
(74) *Attorney, Agent, or Firm* — Morrison & Foerster LLP

(57) ABSTRACT

Neurological diseases, including lysosomal storage diseases, can be successfully treated using intraventricular delivery of the therapeutic agents to bypass the blood-brain barrier. Similarly, diagnostic agents and anesthetic agents can be delivered to the brain in this manner. The administration can be performed slowly to achieve maximum effect. Such administration permits greater penetration of distal portions of the brain.

15 Claims, 8 Drawing Sheets

(56) References Cited

OTHER PUBLICATIONS

Bijvoet, A.G. et al. (Jan. 1998). "Generalized Glycogen Storage and Cardiomegaly in a Knockout Mouse Model of Pompe Disease," *Hum. Mol. Genet.* 7(1):53-62.

Chang, M. et al. (May 2006). "218. Gene Therapy and Enzyme Replacement in a Mouse Model of Late Infantile Neuronal Ceroid Lipofuscinosis," *Molecular Therapy* 13(S1):S84.

Chian, R. et al. (Sep. 1, 2009). "IGE-1:Tetanus Toxin Fragment C Fusion Protein Improves Delivery of IGF-1 to Spinal Cord but Fails to Prolong Survival of ALS Mice," *Brain Research* 1287:1-19.

Cho, S.K. et al. (2005). "Characterization of Lipid-Linked Oligosaccharide Accumulation in Mouse Models of Batten Disease," *Glycobiology* 15(6):637-648.

Clarke, L.A. et al. (1997). "Murine Mucopolysaccharidosis Type I: Targeted Disruption of the Murine α-L-Iduronidase Gene," *Hum. Mol. Genet.* 6(4):503-511.

Dodge, J.C. et al. (2009, e-pub. Nov. 14, 2008). "Intracerebroventricular Infusion of Acid Sphingomyelinase Corrects CNS Manifestations in a Mouse Model of Niemann-Pick A Disease," *Experimental Neurology* 215:349-357.

Dore, S. at al. (Aug. 1997). "Rediscovering an Old Friend, IGF-1: Potential Use in the Treatment Neurodegenerative Diseases," *Trends in Neurosciences* 20(8):326-331.

European Office Action dated Dec. 23, 2010, for EP Application No. 07750236.7, filed on Feb. 8, 2007, six pages.

European Office Action dated Jun. 26, 2012, for EP Application No. 07750236.7, filed on Feb. 8, 2007, four pages.

Final Office Action dated Feb. 22, 2018, for U.S. Appl. No. 12/187,896, filed Aug. 7, 2008, 7 pages.

Final Office Action dated Dec. 27, 2017, for U.S. Appl. No. 14/559,851, filed on Dec. 3, 2014, 10 pages.

Final Office Action dated Apr. 23, 2014, for U.S. Appl. No. 12/175,610, filed Jul. 18, 2008, 5 pages.

Final Office Action dated Dec. 9, 2010, for U.S. Appl. No. 12/187,896, filed Aug. 7, 2008, 11 pages.

Final Office Action dated Feb. 10, 2017, for U.S. Appl. No. 12/187,896, filed Aug. 7, 2008, 7 pages.

Final Office Action dated Jan. 16, 2015, for U.S. Appl. No. 12/187,896, filed Aug. 7, 2008, 9 pages.

Final Office Action dated Jan. 26, 2017, for U.S. Appl. No. 14/559,851, filed Dec. 3, 2014, 16 pages.

Final Office Action dated Sep. 1, 2010, for U.S. Appl. No. 12/175,610, filed Jul. 18, 2008, 17 pages.

Fisher, K.J. et al. (Mar. 1, 1996). "Recombinant Adenovirus Deleted of All Viral Genes for Gene Therapy of Cystic Fibrosis," *Virology* 217(1):11-22.

Franz, C.F. et al. (Mar. 2009, e-pub Dec. 24, 2008). "Intraspinal Cord Delivery of IGF-1 Mediated by Adeno Associated Virus 2 is Neuroprotective in a rat Model of Familial ALS," *Neurobiology of Disease* 33(3):473-481.

Godel, V. et al. (1978). "Visual Functions in Tay Sachs Diseased Patients Following Enzyme Replacement Therapy," *Metab. Ophthalmol.* 2:27-32.

Grondin, R. et al. (Oct. 1, 2002). "Chronic, Controlled GDNF Infusion Promotes Structural and Functional Recovery in Advanced Parkinsonian Monkeys," *Brain* 125(10):2191-2201.

Horinouchi, K. et al. (Jul. 1995). "Acid Sphingomyelinase Deficient Mice: A Model of Types A and B Niemann-Pick Disease," *Nature Genetics* 10:288-293.

International Search Report dated Nov. 16, 2007, for Parent Application No. PCT/US2007/001566 filed Jan. 22, 2017, 3 pages.

International Search Report dated Oct. 16, 2007, for PCT Patent Application No. PCT/US2007/003382, filed Feb. 8, 2007, 2 pages.

International Search Report dated Sep. 26, 2008, for PCT Patent Application No. PCT/US2007/01599, filed Jan. 22, 2007, 2 pages.

Jin, H. K. et al. (May 1, 2002). "Intracerebral Transplantation of Mesenchymal Stem Cells into Acid Sphingomyelinase-Deficient Mice Delays the Onset of Neurological Abnormalities and Extends Their Life Span," *J. Clin. Invest.* 109(9):1183-1191.

Jin, H-K. et al. (Dec. 2003). "Ex Vivo Gene Therapy Using Bone Marrow-Derived Cells: Combines Effects of Intracerebral and Intravenous Transplantation in a Mouse Model of Niemann-Pick Disease," *Molecular Therapy* 8(6):876-885.

Jolly, D. (Mar. 1994). "Viral Vector Systems for Gene Therapy," *Cancer Gene Therapy* 1(1):51-64.

Kakkis, E. et al. (Sep.-Oct. 2004). "Intrathecal Enzyme, Replacement Therapy Reduces Lysosomal Storage in the Brain and Meninges of the Canine Models of MPS1," *Molecular Genetics and Metabolism* 83(1-2):163-174.

Kaspar, K. et al. (Aug. 8, 2003). "Retrograde Viral Delivery of IGF-1 Prolongs survival in a Mouse ALS Model," *Science*, 301(5634):839-842.

Katz, M.L. et al. (Aug. 1999). "A Mouse Gene Knockout Model For Juvenile Ceroid-Lipofuscinosis (Batten Disease)," *J. Neurosci. Res.* 57(4):551-556.

Kochanek, S.et al. (Jun. 1996). "A New Adenoviral Vector: Replacement of All Viral Coding Sequences with 28 Kb of DNA Independently Expressing Both Full-Length Dystrophin and Beta-Galactosidase," *Proc. Natl. Acad. Sci.* USA 93(12):5731-5736.

Kotin, R. M. et al. (Mar. 1, 1990). "Site-Specific Integration by Adeno-Associated Virus," *Proc. Natl. Acad. Sci.* 87(6):2211-2215.

Leventhal, A.R. et al. (Nov. 30, 2001). "Acid Sphingomyelinase-Deficient Macrophages Have Defective Cholesterol Trafficking and Efflux," *J. Biol. Chem.* 276(48):44976-44983.

Lieber, A. et al. (Dec. 1996). "Recombinant Adenoviruses with Large Deletions Generated by Cre-Mediated Excision Exhibit Different Biological Properties Compared with First-Generation Vectors In Vitro and In Vivo," *J. Virol.* 70(12):8944-8960.

Lonser, R. R. at al. (Apr. 2005). "Convection Perfusion of Glucocerebrosidase for Neuronopathic Gaucher's Disease", *Ann. Neurology* 57(4):542-548.

Macauley, S.L. et al. (2009, e-pub. Apr. 8, 2009). "Promising CNS-Directed Enzyme Replacement Therapy for Lysosomal Storage Diseases," *Experimental Neurology* 218:5-8.

Menon, K.P. et al. (Nov. 1992). "Architecture of the Canine *IDUA* Gene and Mutation Underlying Canine Mucopolysaccharidosis I," *Genomics* 14(3):763-768.

Miller, A.D. (Jun. 11, 1992). "Human Gene Therapy Comes of Age" *Nature* 357(6378):455-460.

Miranda, S. et al. (Oct. 2000). "Infusion of Recombinant Human Acid Sphingomyelinase into Niemann-Pick Disease Mice Leads to Visceral, but Not Neurological, Correction of the Pathophysiology", *FASEB J.* 14:1988-1995.

Morral, N. et al. (Dec. 10, 1998). "High Doses of a Helper-Dependent Adenoviral Vector Yield Supraphysiological Levels of $\alpha_1$-Antitrypsin with Negligible Toxicity," *Hum. Gene Ther.* 9(18):2709-2716.

Muenzer, J. et al. (2002). "Enzyme Replacement Therapy in Mucopolysaccharidosis Type II (Hunter Syndrome): A Preliminary Report," *Acta Pasdiatr Suppl* 439:98-99.

Muzyczka, N. (1992). "Use of Adeno-Associated Virus as a General Transduction Vector For Mammalian Cells," *N. Curr. Top. Micro. Immunol.* 158:97-129.

Nagaraja,T.N et al. (Jul. 26, 2005). "In Normal Rat, Intraventricularly Administered Insulin-Like Growth Factor is Rapidly Cleared from CSF with Limited Distribution into Brain," *Cerebrospinal Fluid Research* 2(5):1-15.

Non-Final Office Action dated Apr. 21, 2016, for U.S. Appl. No. 12/187,896, filed Aug. 7, 2008, 7 pages.

Non-Final Office Action dated Aug. 4, 2017, for U.S. Appl. No. 12/187,896, filed Aug. 7, 2008, 7 pages.

Non-Final Office Action dated Aug. 7, 2017, for U.S. Appl. No. 14/559,851, filed Dec. 3, 2014, 10 pages.

Non-Final Office Action dated Jun. 20, 2014, for U.S. Appl. No. 12/187,896, filed Aug. 7, 2008, 9 pages.

Non-Final Office Action dated Mar. 30, 2010, for U.S. Appl. No. 12/187,896, filed Aug. 7, 2008, 12 pages.

Non-Final Office Action dated Mar. 5, 2010, for U.S. Appl. No. 12/175,610, filed Jul. 18, 2008, 13 pages.

Non-Final Office Action dated May 19, 2016, for U.S. Appl. No. 14/559,851, filed Dec. 3, 2014, 14 pages.

(56) References Cited

OTHER PUBLICATIONS

Non-Final Office Action dated Oct. 16, 2013, for U.S. Appl. No. 12/175,610, filed Jul. 18, 2008, 9 pages.
Notice of Allowance dated May 23, 2018, for U.S. Appl. No. 14/559,851, filed Dec. 3, 2014, 9 pages.
Otterbach, B. et al. (Jun. 30, 1995). "Acid Sphingomyelinase-Deficient Mice Mimic the Neurovisceral Form of Human Lysosomal Storage Disease (Niemann-Pick Disease)," *Cell* 81(7):1053-1061.
Parks, R.J. et al. (Nov. 26, 1996). "A Helper-Dependent Adenovirus Vector System Removal of Helper Virus by Cre-Mediated Excision of the Viral Packaging Signal," *Proc. Natl. Acad. Sci. USA* 93(24):13565-13570.
Ponnazhagan, S. et al. (Feb. 10, 1997). "Lack of Site-Specific Integration of the Recombinant Adeno-Associated Virus 2 Genomes in Human Cells," *Hum Gene Ther.* 8(3):275-284.
Qiu, H. et al. (Aug. 29, 2003). "Activation of Human Acid Sphingomyelinase through Modification or Deletion of C-terminal Cysteine," *J. Biol. Chem.* 278(35):32744-32752.
Raben, N. et al. (Oct. 2003). "Enzyme Replacement Therapy in the Mouse Model of Pompe Disease" *Mol. Genet. Metab.* 80(1-2):159-169.
Restriction Requirement dated Sep. 3, 2009, for U.S. Appl. No. 12/175,610, filed Jul. 18, 2008, 6 pages.
Sano, Y. (Dec. 10, 1988). "Morphological Aspects of the Blood-Brain Barrier—A Historical Review," *Advances in Neurological Sciences* 32(6):953-965.
Schuchman, E. et al. (2001). "Niemann-Pick Disease Types A and B: Acid Sphingomyelinase Deficiencies," Chapter 144 in *The Metabolic and Molecular Bases of Inherited Diseases*, Scriver, et al. eds., McGraw-Hill, pp. 3589-3610.
Schuchman, E. et al. (May 5, 1991). "Human acid sphingomyelinase. Isolation, Nucleotide Sequence and Expression of the Full-Length and Alternatively Spliced cDNAs," J. Biol. Chem. 266(13):8531-8539.

Shen, D. D. et al. (Oct. 2004). "Principles and Applicability of CSF Sampling for the Assessment of CNS Drug Delivery and Pharmacodynamics," *Advanced Drug Delivery Reviews* 56(12):1825-1857.
Slotte, J.P. (1997). "Cholesterol-Sphingomyelin Interactions in Cells—Effects on Lipid Metabolism," *Subcell. Biochem.* 28:277-293.
Sorensen, E.J. et al. (Nov. 25, 2008). "Subcuteneous IGF-1 is Not Beneficial in 2-year ALS Trial," *Neurology* 71:(22):770-1776, 6 pages.
Stedman, T. L. (1995). *Stedman's Medical Dictionary*, Williams & Wilkins Baltimore 26:220, 1 page.
Stedman's Medical Dictionary, 26th edition, p. 1951.
Viana, M.B. et al. (1990). "Very Low Levels of High Density Lipoprotein Cholesterol in Four Sibs of a Family with Non-Neuropathic Niemann-Pick disease and Sea-Blue Histiocytosis," *J. Med. Genet.* 27:499-504.
Von Specht, B.U. et al. (Jun. 1, 1979). "Enzyme Replacement in Tay-Sachs Disease," *Neurology* 29:848-854.
Written Opinion of the International Searching Authority dated Nov. 16, 2007, for Patent Application No. PCT/US2007/001566, filed Jan. 22, 2007, 6 pages.
Written Opinion of the International Searching Authority dated Oct. 16, 2007, for PCT Patent Application No. PCT/US2007/003382, filed Feb. 8, 2007, 5 pages.
Written Opinion of the International Searching Authority dated Sep. 26, 2008, for PCT Patent Application No. PCT/US2007/01599, filed Jan. 22, 2007, 6 pages.
Xu, Y. et al. (Nov. 2003). "Viable Mouse Models of Acid β-Glucosidase Deficiency: The Defect in Gaucher Disease," *Am. J. Pathol.* 163(5):2093-2101.
Ziegler, R.J. et al. (2011, e-pub. Jul. 14, 2011). "Distribution of Acid Sphingomyelinase in Rodent and Non-Human Primate Brain After Intracerebroventricular Infusion," *Experimental Neurology* 231:261-271.

FIG. 7

| | Known | variants | | | |
|---|---|---|---|---|---|
| VARIANT | 157 | 1 | C -> R | (seems to be less active). |
| VARIANT | 242 | 1 | G -> R | (in NPB). |
| VARIANT | 246 | 1 | E -> Q | (in NPA; 30% residual activity). |
| VARIANT | 248 | 1 | S -> R | (in NPA). |
| VARIANT | 302 | 1 | L -> P | (in NPA; in 23% of NPA Ashkenazi Jewish patients). |
| VARIANT | 319 | 1 | H -> Y | (in NPA). |
| VARIANT | 371 | 1 | P -> S | (in NPB). |
| VARIANT | 382 | 1 | M -> I | (in NPA). |
| VARIANT | 383 | 1 | N -> S | (in NPB). |
| VARIANT | 389 | 1 | N -> T | (in NPA). |
| VARIANT | 391 | 1 | W -> G | (in NPB; low sphingomyelin degradation rates). |
| VARIANT | 421 | 1 | H -> Y | (in NPB). |
| VARIANT | 436 | 1 | S -> R | (in NPB). |
| VARIANT | 446 | 1 | Y -> C | (in NPA). |
| VARIANT | 463 | 1 | F -> S | (in NPA). |
| VARIANT | 475 | 1 | P -> L | (in NPA). |
| VARIANT | 496 | 1 | R -> L | (in NPA; in 32% of NPA Ashkenazi Jewish patients). |
| VARIANT | 537 | 1 | Y -> H | (in NPA). |
| VARIANT | 577 | 1 | G -> S | (in NPA). |
| VARIANT | 608 | 1 | Missing | (in NPB; prevalent among NPB patients from the North-African Maghreb region). |

SLOW INTRAVENTRICULAR DELIVERY

CROSS-REFERENCE TO RELATED APPLICATIONS

This application is a continuation of U.S. patent application Ser. No. 12/187,896, filed Aug. 7, 2008, which is a continuation of PCT Application No. PCT/US2007/03382, filed Feb. 8, 2007, which claims priority under 35 U.S.C. § 119 (e) to U.S. Provisional Application No. 60/771,451 filed, Feb. 9, 2006, the disclosures of which are hereby incorporated by reference in their entirety.

TECHNICAL FIELD OF THE INVENTION

This invention is related to delivery of agents to the brain. In particular it relates to brain diagnosis, treatment, and imaging.

A group of metabolic disorders known as lysosomal storage diseases (LSD) includes over forty genetic disorders, many of which involve genetic defects in various lysosomal hydrolases. Representative lysosomal storage diseases and the associated defective enzymes are listed in Table 1.

TABLE 1

| Lysosomal storage disease | Defective enzyme |
| --- | --- |
| Aspartylglucosaminuria | Aspartylglucosaminidase |
| Fabry | .alpha.-Galactosidase A |
| Infantile Batten Disease* (CNL1) | Palmitoyl Protein Thioesterase |
| Classic Late Infantile Batten Disease* (CNL2) | Tripeptidyl Peptidase |
| Juvenile Batten Disease* (CNL3) | Lysosomal Transmembrane Protein |
| Batten, other forms* (CNL4-CNL8) | Multiple gene products |
| Cystinosis | Cysteine transporter |
| Farber | Acid ceramidase |
| Fucosidosis | Acid .alpha.-L-fucosidase |
| Galactosidosialidosis | Protective protein/cathepsin A |
| Gaucher types 1, 2*, and 3* | Acid .beta.-glucosidase, or |
| G.sub.M1 gangliosidosis* | Acid .beta.-galactosidase |
| Hunter* | Iduronate-2-sulfatase |
| Hurler-Scheie* | .alpha.-L-Iduronidase |
| Krabbe* | Galactocerebrosidase. |
| alpha.-Mannosidosis* | Acid .alpha.-mannosidase |
| beta.-Mannosidosis* | Acid .beta.-mannosidase |
| Maroteaux-Lamy | Arylsulfatase B |
| Metachromatic leukodystrophy* | Arylsulfatase A |
| Morquio A | N-Acetylgalactosamine-6-sulfate |
| Morquio B | Acid .beta.-galactosidase |
| Mucolipidosis II/III* | N-Acetylglucosamine-1- |
| Niemann-Pick A*, B | Acid sphingomyelinase |
| Niemann-Pick C* | NPC-1 |
| Pompe* | Acid .alpha.-glucosidase |
| Sandhoff* | .beta.-Hexosaminidase B |
| Sanfilippo A* | Heparan N-sulfatase |
| Sanfilippo B* | .alpha.-N-Acetylglucosaminidase |
| Sanfilippo C* | Acetyl-CoA: alpha.-glucosaminide |
| Sanfilippo D* | N-Acetylglucosamine-6-sulfate |
| Schindler Disease* | .alpha.-N-Acetylgalactosaminidase |
| Schindler-Kanzaki. | alpha.-N-Acetylgalactosaminidase |
| Sialidosis | .alpha.-Neuramidase |
| Sly* | .beta.-Glucuronidase |
| Tay-Sachs* | .beta.-Hexosaminidase A |
| Wolman* | Acid Lipase |

*CNS involvement

The hallmark feature of LSD is the abnormal accumulation of metabolites in the lysosomes which leads to the formation of large numbers of distended lysosomes in the perikaryon. A major challenge to treating LSD (as opposed to treating a liver-specific enzymopathy) is the need to reverse lysosomal storage pathology in multiple separate tissues. Some LSDs can be effectively treated by intravenous infusion of the missing enzyme, known as enzyme replacement therapy (ERT). For example, Gaucher type 1 patients have only visceral disease and respond favorably to ERT with recombinant glucocerebrosidase (Cerezyme™, Genzyme Corp.). However, patients with metabolic disease that affects the CNS (e.g., type 2 or 3 Gaucher disease) partially respond to intravenous ERT because the replacement enzyme is prevented from entering the brain by the blood brain barrier (BBB). Furthermore, attempts to introduce a replacement enzyme into the brain by direct injection have been limited in part due to enzyme cytotoxicity at high local concentrations and limited parenchymal diffusion rates in the brain (Partridge, Peptide Drug Delivery to the Brain, Raven Press, 1991).

According to UniProtKB/Swiss-Prot entry P17405, defects in the SMPD1 gene, located on chromosome 11, (11p15.4-p15.1), are the cause of Niemann-Pick disease type A (NPA), also referred to as the classical infantile form. Niemann-Pick disease is a clinically and genetically heterogeneous recessive disorder. It is caused by the accumulation of sphingomyelin and other metabolically related lipids in the lysosomes, resulting in neurodegeneration starting from early life. Patients may show xanthomas, pigmentation, hepatosplenomegaly, lymphadenopathy and mental retardation. Niemann-Pick disease occurs more frequently among individuals of Ashkenazi Jewish ancestry than in the general population. NPA is characterized by very early onset in infancy and a rapidly progressive course leading to death by three years. The acid sphingomyelinase enzyme (aSM) converts sphingomyelin to ceramide. aSM also has phospholipase C activities toward 1,2-diacylglycerolphosphocholine and 1,2-diacylglycerolphosphoglycerol. The enzyme converts

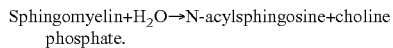

Sphingomyelin+$H_2O$→N-acylsphingosine+choline phosphate.

There is a continuing need in the art for methods to treat LSDs that have both cerebral and visceral disease pathologies. There is a continuing need in the art for methods to access portions of the brain with diagnostic and therapeutic agents that do not readily cross the blood-brain barrier.

SUMMARY OF THE INVENTION

According to one embodiment of the invention a method is provided of delivering an agent to a patient's brain. The agent is administered to the patient via a lateral ventricle of the brain at a rate such that the administration of a single dose consumes more than two hours.

According to another embodiment of the invention a method is provided of delivering an agent to a patient's brain. The agent is administered to the patient via a lateral ventricle of the brain at a rate such that the administration of a single dose consumes at least 50% of the turn-over time of the cerebrospinal fluid in the patient.

According to still another embodiment of the invention a method is provided of delivering an agent to a patient's brain. Turn-over time of cerebrospinal fluid of the patient is estimated. A rate for delivery and a total delivery time of the agent via a lateral ventricle of the brain is selected based on the turn-over time. A pump is set to deliver the agent at said selected rate for said total delivery time.

According to yet another embodiment of the invention a method is provided of delivering an agent to a patient's brain. Turn-over time of cerebrospinal fluid of the patient is estimated. A rate and a total delivery time is selected for delivery of the agent via a lateral ventricle of the brain based on the turn-over time. The agent is delivered to the patient at said selected rate for said total delivery time.

According to another aspect of the invention a method is provided of delivering an agent to a patient's brain. The agent is administered to the patient via a lateral ventricle of the brain at a rate such that the administration of a single dose continues at least until the agent is detectable in serum of the patient.

According to one embodiment of the invention a patient with Niemann-Pick A or B disease is treated. An acid sphingomyelinase is administered to the patient via intraventricular delivery to the brain in an amount sufficient to reduce sphingomyelin levels in said brain.

Another aspect of the invention is a kit for treating a patient with Niemann-Pick A or B disease. The kit comprises an acid sphingomyelinase, and a catheter for delivery of said acid sphingomyelinase to the patient's brain ventricles.

Yet another aspect of the invention is a kit for treating a patient with Niemann-Pick A or B disease. The kit comprises an acid sphingomyelinase and a pump for delivery of said acid sphingomyelinase to the patient's brain ventricles.

According to the invention a patient can be treated who has a lysosomal storage disease which is caused by an enzyme deficiency which leads to accumulation of the enzyme's substrate. The enzyme is administered to the patient via intraventricular delivery to the brain. The rate of administration is such that the administration of a single dose consumes more than four hours. Substrate levels in said brain are thereby reduced.

These and other embodiments which will be apparent to those of skill in the art upon reading the specification provide the art with methods for delivering agents to hard-to-reach portions of the brain.

BRIEF DESCRIPTION OF THE DRAWINGS

FIG. 7 shows documented hASM variants and their relationship to disease or enzyme activity.

DETAILED DESCRIPTION OF THE INVENTION

Figure 1:
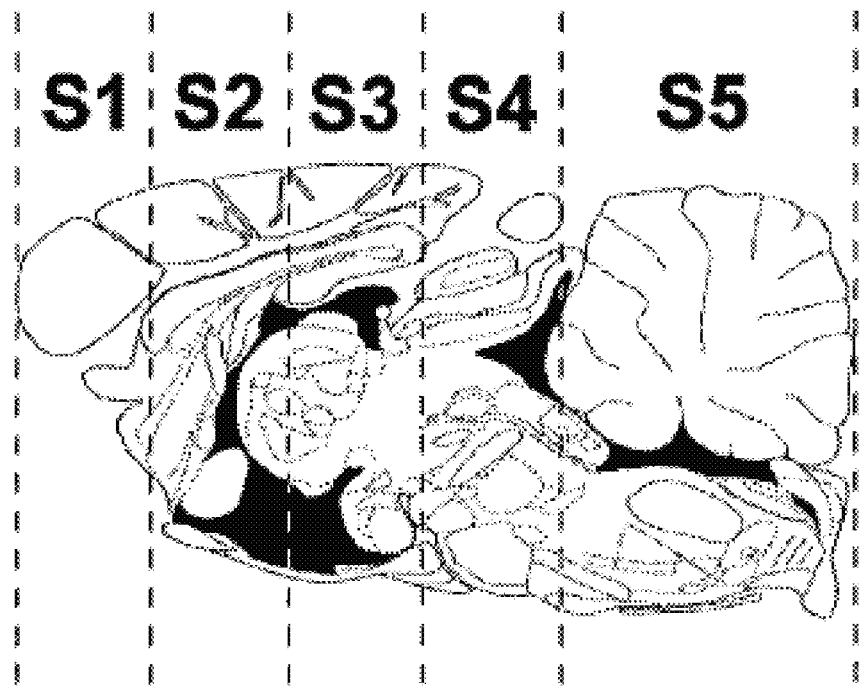
FIG. 1 shows diagram of sections of brain that were analyzed for sphingomyelin. S1 is at the front of brain and S5 is at the back of brain.
Figure 2:
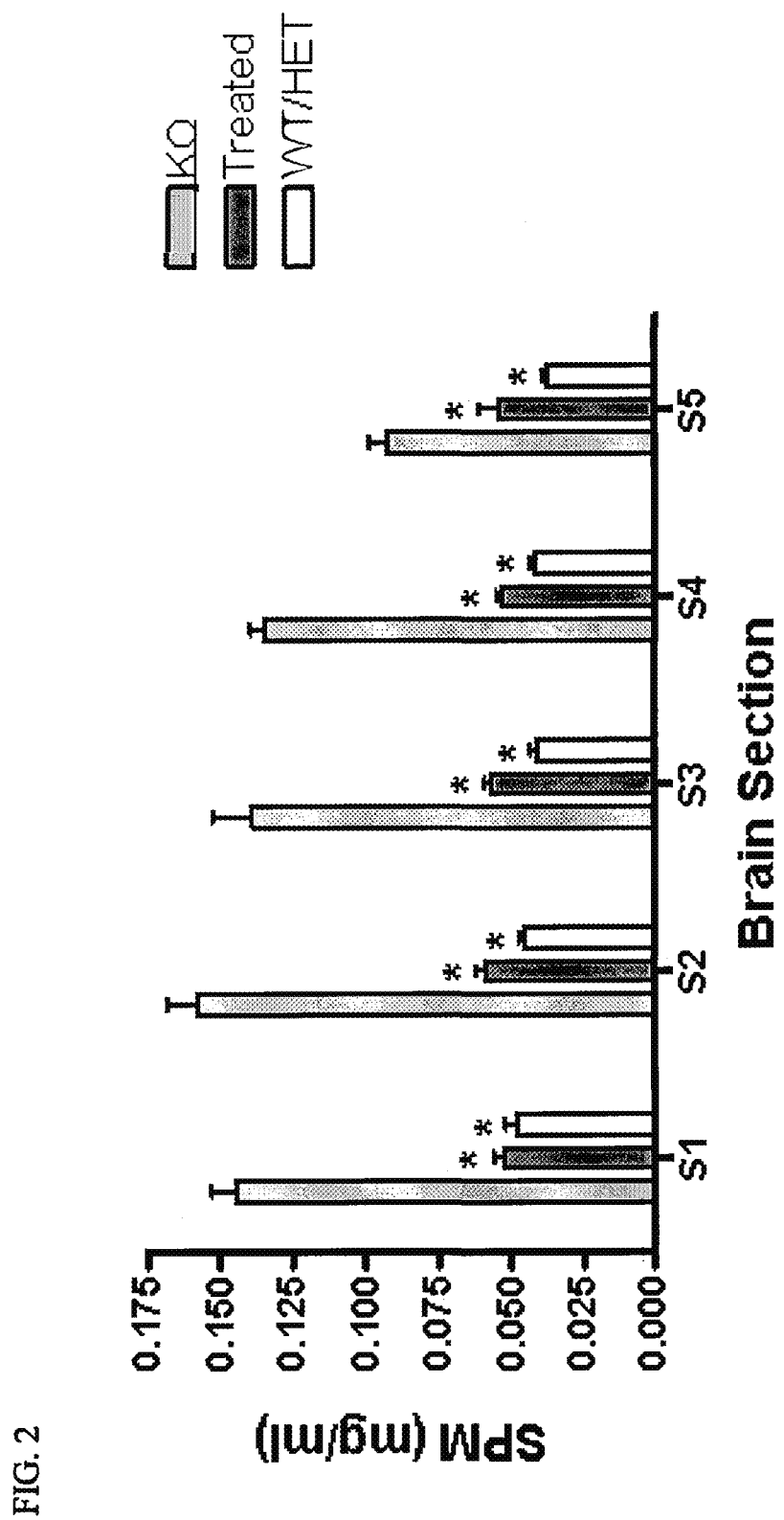
FIG. 2 shows that intraventricular administration of rhASM reduces SPM levels in the ASMKO mouse brain.
Figure 3:
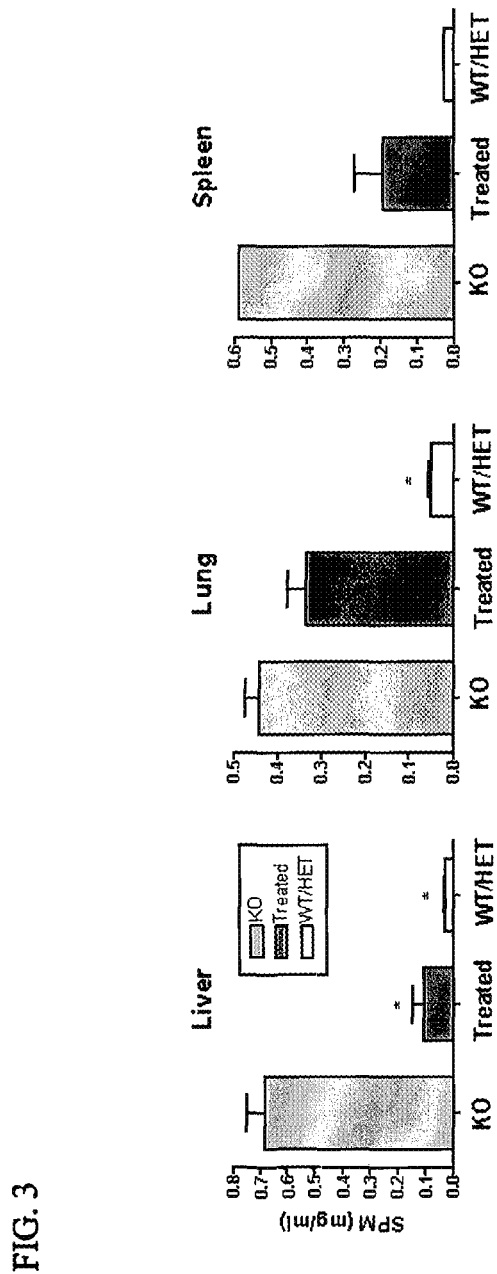
FIG. 3 shows intraventricular administration of rhASM reduces SPM levels in the ASMKO liver, spleen, and lung.
Figure 4:
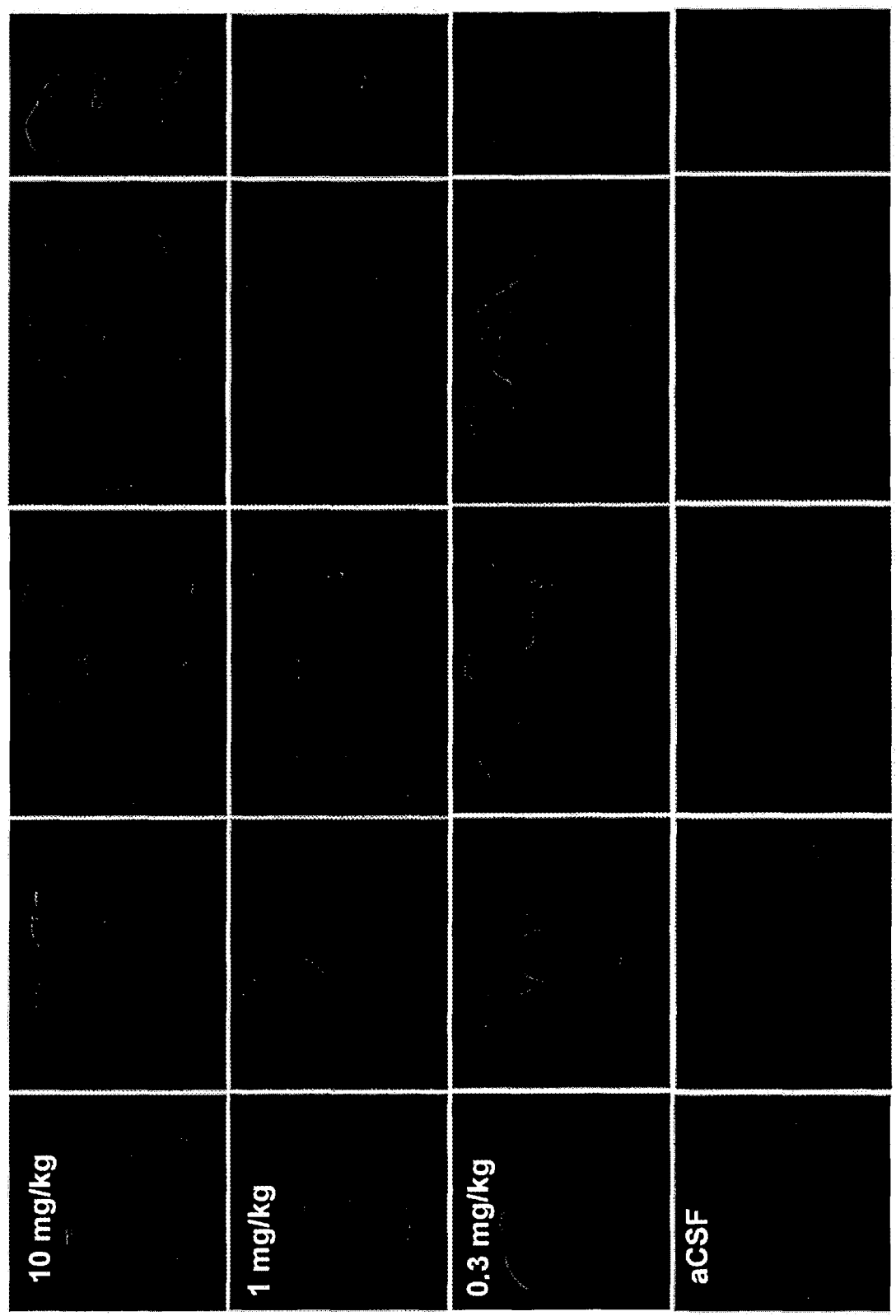
FIG. 4 shows hASM staining in the brain following intraventricular infusion.
Figure 5:
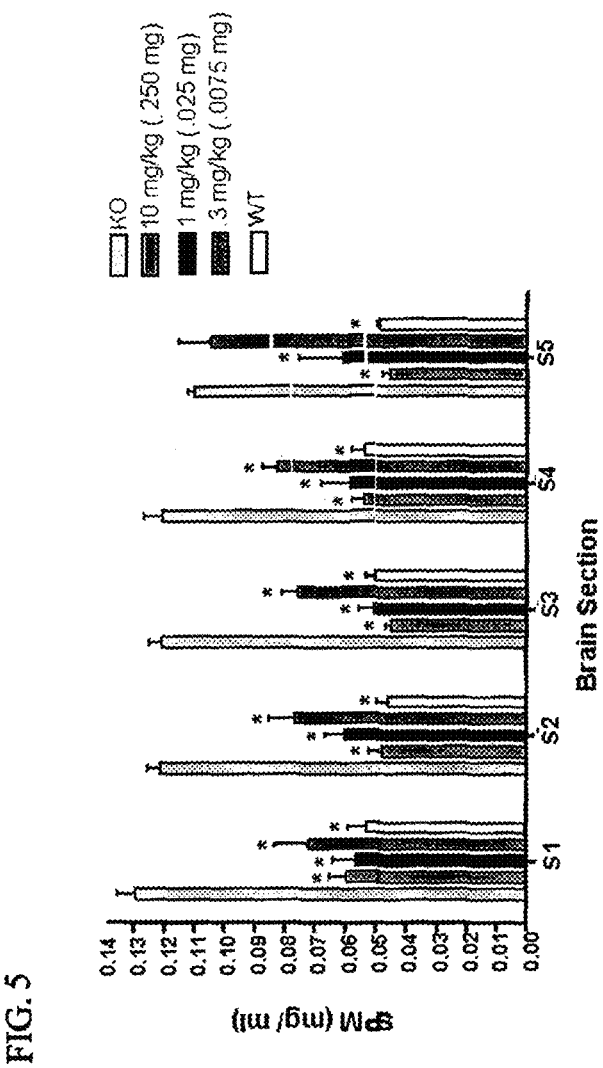
FIG. 5 shows that intraventricular infusion of rhASM over a 6 h period reduces SPM levels in the ASMKO mouse brain.
Figure 6:
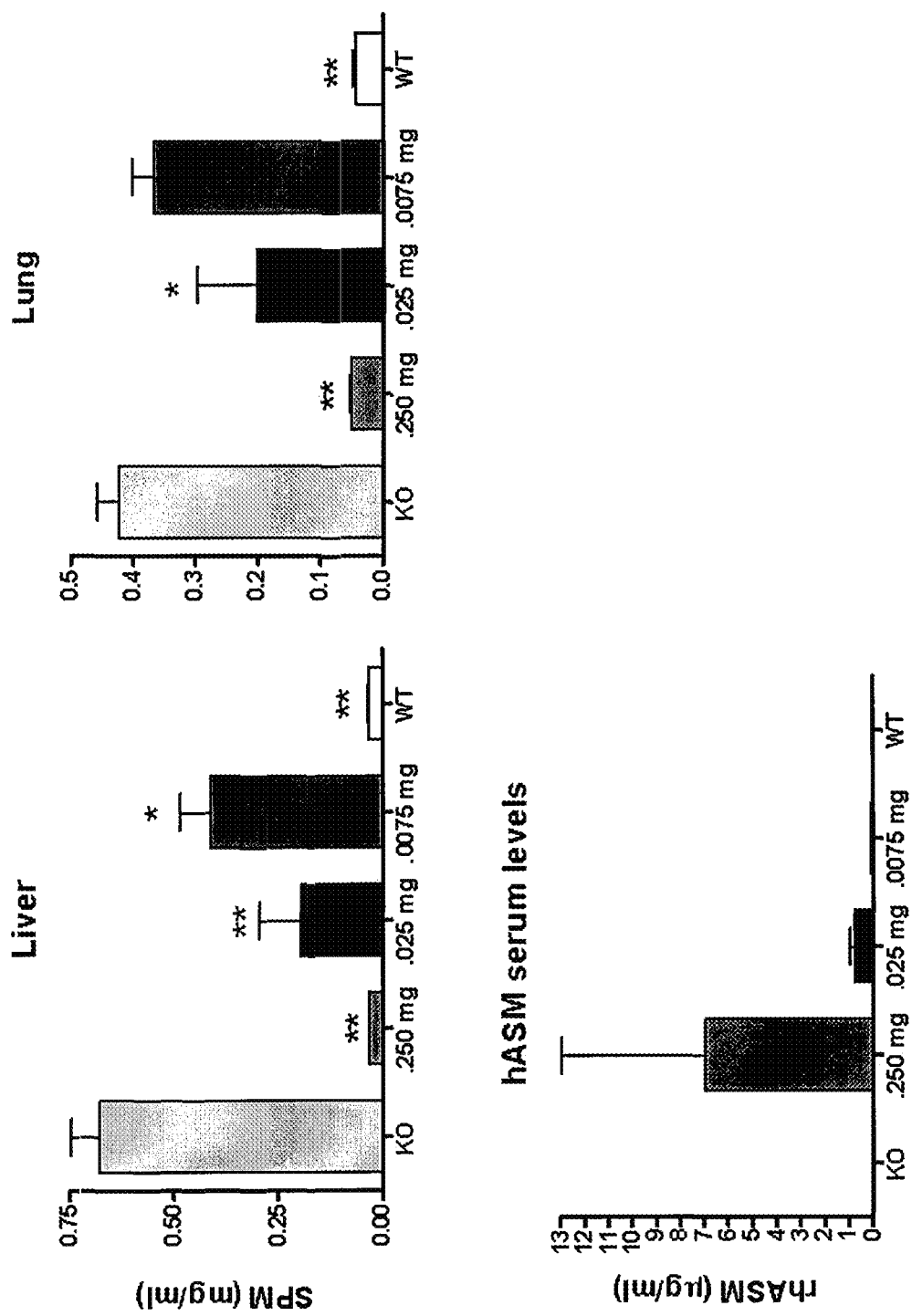
FIG. 6 shows that intraventricular infusion of rhASM over a 6 h period reduces SPM levels in ASMKO liver, serum, and lung.
Figure 8:
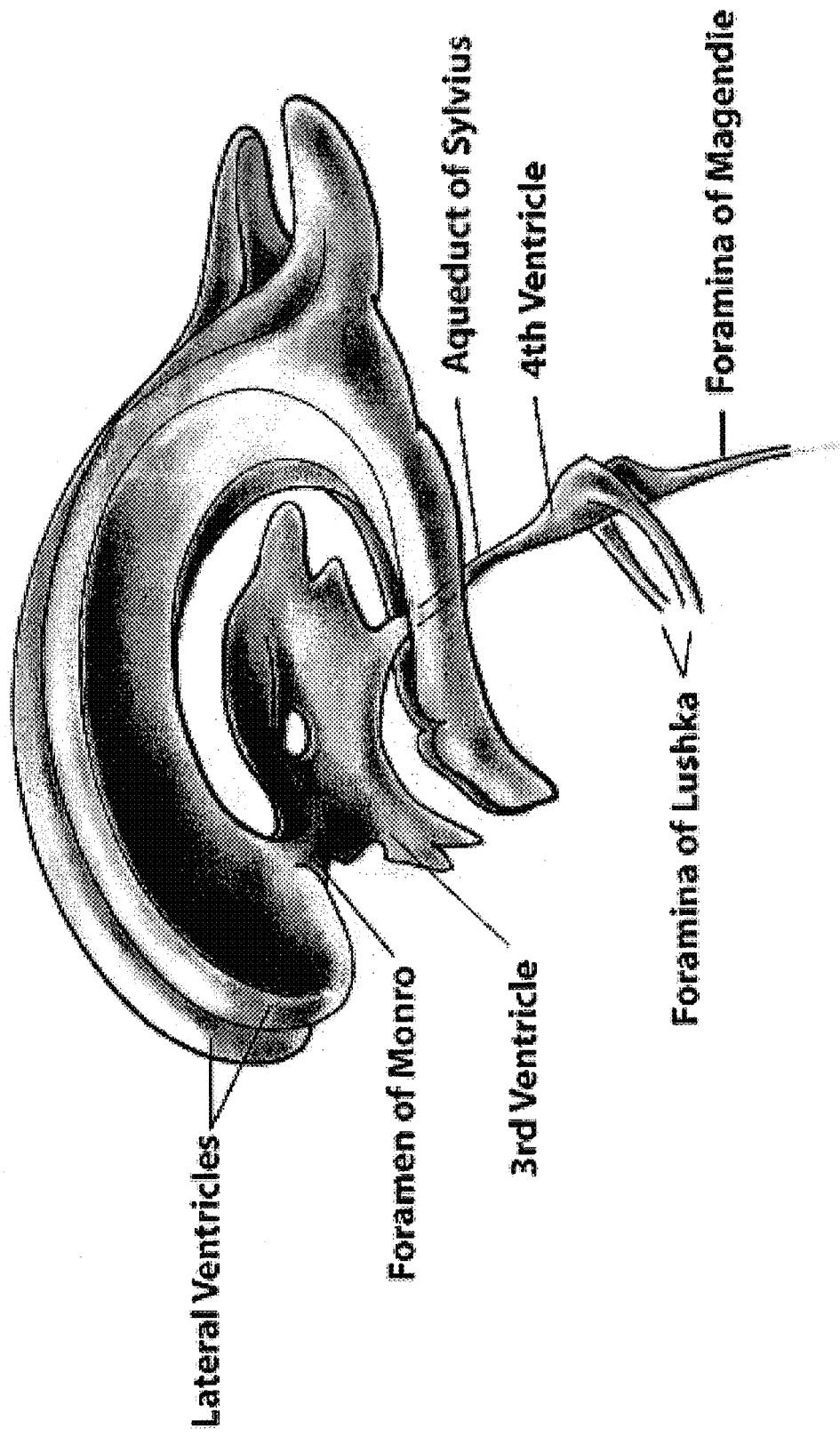
FIG. 8 shows the ventricular system which bathes the entire brain and spinal cord with cerebrospinal fluid.

The inventors have discovered that intraventricular delivery of agents to patients at a slow rate, rather than in a bolus delivery, increases the effective penetration of the agents to distal portions of the brain from the site of introduction. Agents which can be administered in this manner are any, but include diagnostic agents, imaging agents, anesthetic agents, and therapeutic agents. This mode of delivery is particularly useful for agents which cannot cross the blood-brain barrier.

Applicants have observed that bolus intraventricular administration is not very effective, whereas slow infusion is very effective. While applicants do not wish to be bound by any particular theory of operation, it is believed that the slow infusion is effective due to the turn-over of the cerebrospinal fluid (CSF). While estimates and calculations in the literature vary, the adult human cerebrospinal fluid is believed to turn over within about 4, 5, 6, 7, or 8 hours. The turn-over rate may vary depending on the size of the individual and the volume of cerebrospinal fluid in the individual. Thus for example, children have less cerebrospinal fluid than adults and therefore have a shorter turn-over time. The slow infusion of the invention can be metered so that the delivery time is about equal to or greater than the turn-over time of the CSF. The metering can be a fixed time, for example, greater than 2, 4, 6, 8, or 10 hours, or it can be set to be a fraction of the estimated turn-over time, for example greater than 50%, 75%, 100%, 150%, 200%, 300%, or 400%. The CSF empties into the venous blood system. The delivery can be performed for a time until the delivered agent is detectable in the serum of the patient. One can also detect and/or measure delivered agent in other parts of the CNS such as in the spinal cord and the subarachnoid space. These, too, can be used as endpoints for delivery.

CSF is secreted at a rate of about 430 to 600 ml/day or about 0.35 to 0.4 per minute in adults and the volume at any given moment is approximately 80 to 150 ml, with the entire volume being replaced every six to eight hours. Infants are estimated to produce 0.15 ml per minute. The choroid plexuses of the lateral ventricals are the largest and produce most of the CSF. The fluid flows through the intraventricular foramina in the third ventricle, is augmented by fluid formed in the choroid plexus of that ventricle, and passes through the cerebral aqueduct of Sylvius to the fourth ventricle. CSF flows from 4th ventricle to foramen of Magendie to the sub-arachnoid space that surrounds the spinal cord; CSF flows from 4th ventricle to the foramen of Lusaka to the sub-arachnoid space that surrounds the brain. The arachnoid membrane lines the sub-arachnoid space; arachnoid villi are part of the membrane. Arachnoid villi are pumps that take in the CSF and return it to the venous circulation. The CSF is reabsorbed into the blood through the arachnoid villi.

Slower-than-bolus delivery according to the invention has the advantage of delivering agents to portions of the brain that are not reached with a bolus. Bolus-delivered agent accumulates in the ependymal layer or in the parenchyma adjacent to the injection site. In contrast, slow-delivered agents are found to access distal regions of the parenchyma from the injection site (widespread delivery across the anterior-to-posterior axis of the brain; in addition widespread delivery dorsally and ventrally to the ependymal layer), the third ventricle, the Aqueduct of Sylvius, the fourth ventricle, the Foramina of Lushka, the Foramina of Magendie, the spinal cord, the subarachnoid space, and the serum. From the serum, peripheral organs can also be reached.

The CSF empties into the blood via the arachnoid villi and intracranial vascular sinuses, thereby delivering the enzymes to the visceral organs. The visceral organs which are often affected in Niemann-Pick disease are the lungs, spleen, kidney, and liver. The slow intraventricular infusion provides diminished amounts of substrate in at least these visceral organs.

The reduction in substrate accumulated in the brain, lungs, spleen, kidney, and/or liver is dramatic. Reductions of greater that 10%, 20%, 30%, 40%, 50%, 60%, 70%, 80%, 90% can be achieved. The reduction achieved is not necessarily uniform from patient to patient or even from organ to organ within a single patient.

Agents for delivery can be any that are known in the art for treatment and imaging of brains. Imaging agents can be radioactive, radio-opaque, fluorescent, etc. Therapeutic agents can be any that are useful for treating neurological or other brain diseases. Anesthetics can be for treating chronic or acute pain, for example lidocaine hydrochloride and morphine. Examples of therapeutic agents include the enzymes that are deficient in lysosomal storage diseases. Other possible agents for use include nucleic acid vectors, such as plasmid and viral vectors, siRNA, anti-sense RNAs, etc. Other therapeutic agents include those which increase or decrease excitation of neurons in the brain. These include agonists or antagonists of glutamtate, GABA, and dopamine. Specific examples include cycloserine, carboxyphenylglycine, glutamic acid, dizocilpine, ketamaine, dextromethorphan, baclofen, muscinol, gabazine, saclofen, haloperidol, and methane sulfonate. Additional agents which can be used are anti-inflammatory agents, in particular non-steroidal anti-inflammatory agents such as indomethacin and cyclooxygenase inhibitors.

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

Adenovirus is a non-enveloped, nuclear DNA virus with a genome of about 36 kb, which has been well-characterized through studies in classical genetics and molecular biology (Hurwitz, M. S., Adenoviruses *Virology*, $3^{rd}$ edition, Fields et al., eds., Raven Press, New York, 1996; Hitt, M. M. et al., Adenovirus Vectors, The Development of Human Gene Therapy, Friedman, T. ed., Cold Spring Harbor Laboratory Press, New York 1999). The viral genes are classified into early (designated E1-E4) and late (designated L1-L5) transcriptional units, referring to the generation of two temporal classes of viral proteins. The demarcation of these events is viral DNA replication. The human adenoviruses are divided into numerous serotypes (approximately 47, numbered accordingly and classified into 6 groups: A, B, C, D, E and F), based upon properties including hemaglutination of red blood cells, oncogenicity, DNA and protein amino acid compositions and homologies, and antigenic relationships.

Recombinant adenoviral vectors have several advantages for use as gene delivery vehicles, including tropism for both dividing and non-dividing cells, minimal pathogenic potential, ability to replicate to high titer for preparation of vector stocks, and the potential to carry large inserts (Berkner, K. L., *Curr. Top. Micro. Immunol.* 158:39-66, 1992; Jolly, D., Cancer Gene Therapy 1:51-64 1994). Adenoviral vectors with deletions of various adenoviral gene sequences, such as pseudoadenoviral vectors (PAVs) and partially-deleted adenoviral (termed "DeAd"), have been designed to take advantage of the desirable features of adenovirus which render it a suitable vehicle for delivery of nucleic acids to recipient cells.

In particular, pseudoadenoviral vectors (PAVs), also known as 'gutless adenovirus' or mini-adenoviral vectors, are adenoviral vectors derived from the genome of an adenovirus that contain minimal cis-acting nucleotide sequences required for the replication and packaging of the vector genome and which can contain one or more transgenes (See, U.S. Pat. No. 5,882,877 which covers pseudoadenoviral vectors (PAV) and methods for producing PAV, incorporated herein by reference). PAVs have been designed to take advantage of the desirable features of adenovirus which render it a suitable vehicle for gene delivery. While adenoviral vectors can generally carry inserts of up to 8 kb in size by the deletion of regions which are dispensable for viral growth, maximal carrying capacity can be achieved with the use of adenoviral vectors containing deletions of most viral coding sequences, including PAVs. See U.S. Pat. No. 5,882,877 of Gregory et al.; Kochanek et al., *Proc. Natl. Acad. Sci. USA* 93:5731-5736, 1996; Parks et al., *Proc. Natl. Acad. Sci. USA* 93:13565-13570, 1996; Lieber et al., *J. Virol.* 70:8944-8960, 1996; Fisher et al., *Virology* 217:11-22, 1996; U.S. Pat. No. 5,670,488; PCT Publication No. WO96/33280, published Oct. 24, 1996; PCT Publication No. WO96/40955, published Dec. 19, 1996; PCT Publication No. WO97/25446, published Jul. 19, 1997; PCT Publication No. WO95/29993, published Nov. 9, 1995; PCT Publication No. WO97/00326, published Jan. 3, 1997; Morral et al., *Hum. Gene Ther.* 10:2709-2716, 1998. Such PAVs, which can accommodate up to about 36 kb of foreign nucleic acid, are advantageous because the carrying capacity of the vector is optimized, while the potential for host immune responses to the vector or the generation of replication-competent viruses is reduced. PAV vectors contain the 5' inverted terminal repeat (ITR) and the 3' ITR nucleotide sequences that contain the origin of replication, and the cis-acting nucleotide sequence required for packaging of the PAV genome, and can accommodate one or more transgenes with appropriate regulatory elements, e.g. promoter, enhancers, etc.

Other, partially deleted adenoviral vectors provide a partially-deleted adenoviral (termed "DeAd") vector in which the majority of adenoviral early genes required for virus replication are deleted from the vector and placed within a producer cell chromosome under the control of a conditional promoter. The deletable adenoviral genes that are placed in the producer cell may include E1A/E1B, E2, E4 (only ORF6 and ORF6/7 need be placed into the cell), pIX and pIVa2. E3 may also be deleted from the vector, but since it is not required for vector production, it can be omitted from the producer cell. The adenoviral late genes, normally under the control of the major late promoter (MLP), are present in the vector, but the MLP may be replaced by a conditional promoter.

Conditional promoters suitable for use in DeAd vectors and producer cell lines include those with the following characteristics: low basal expression in the uninduced state, such that cytotoxic or cytostatic adenovirus genes are not expressed at levels harmful to the cell; and high level expression in the induced state, such that sufficient amounts of viral proteins are produced to support vector replication and assembly. Preferred conditional promoters suitable for use in DeAd vectors and producer cell lines include the dimerizer gene control system, based on the immunosuppressive agents FK506 and rapamycin, the ecdysone gene control system and the tetracycline gene control system. Also useful in the present invention may be the Gene-Switch™ technology (Valentis, Inc., Woodlands, Tex.) described in Abruzzese et al., Hum. Gene Ther. 1999 10:1499-507, the disclosure of which is hereby incorporated herein by reference. The partially deleted adenoviral expression system is further described in WO99/57296, the disclosure of which is hereby incorporated by reference herein.

Adeno-associated virus (AAV) is a single-stranded human DNA parvovirus whose genome has a size of 4.6 kb. The AAV genome contains two major genes: the rep gene, which codes for the rep proteins (Rep 76, Rep 68, Rep 52, and Rep 40) and the cap gene, which codes for AAV replication, rescue, transcription and integration, while the cap proteins form the AAV viral particle. AAV derives its name from its dependence on an adenovirus or other helper virus (e.g., herpesvirus) to supply essential gene products that allow AAV to undergo a productive infection, i.e., reproduce itself in the host cell. In the absence of helper virus, AAV integrates as a provirus into the host cell's chromosome, until it is rescued by superinfection of the host cell with a helper virus, usually adenovirus (Muzyczka, Curr. Top. Micor. Immunol. 158:97-127, 1992).

Interest in AAV as a gene transfer vector results from several unique features of its biology. At both ends of the AAV genome is a nucleotide sequence known as an inverted terminal repeat (ITR), which contains the cis-acting nucleotide sequences required for virus replication, rescue, packaging and integration. The integration function of the ITR mediated by the rep protein in trans permits the AAV genome to integrate into a cellular chromosome after infection, in the absence of helper virus. This unique property of the virus has relevance to the use of AAV in gene transfer, as it allows for a integration of a recombinant AAV containing a gene of interest into the cellular genome. Therefore, stable genetic transformation, ideal for many of the goals of gene transfer, may be achieved by use of rAAV vectors. Furthermore, the site of integration for AAV is well-established and has been localized to chromosome 19 of humans (Kotin et al., Proc. Natl. Acad. Sci. 87:2211-2215, 1990). This predictability of integration site reduces the danger of random insertional events into the cellular genome that may activate or inactivate host genes or interrupt coding sequences, consequences that can limit the use of vectors whose integration of AAV, removal of this gene in the design of rAAV vectors may result in the altered integration patterns that have been observed with rAAV vectors (Ponnazhagan et al., Hum Gene Ther. 8:275-284, 1997).

There are other advantages to the use of AAV for gene transfer. The host range of AAV is broad. Moreover, unlike retroviruses, AAV can infect both quiescent and dividing cells. In addition, AAV has not been associated with human disease, obviating many of the concerns that have been raised with retrovirus-derived gene transfer vectors.

Standard approaches to the generation of recombinant rAAV vectors have required the coordination of a series of intracellular events: transfection of the host cell with an rAAV vector genome containing a transgene of interest flanked by the AAV ITR sequences, transfection of the host cell by a plasmid encoding the genes for the AAV rep and cap proteins which are required in trans, and infection of the transfected cell with a helper virus to supply the non-AAV helper functions required in trans (Muzyczka, N., Curr. Top. Micor. Immunol. 158:97-129, 1992). The adenoviral (or other helper virus) proteins activate transcription of the AAV rep gene, and the rep proteins then activate transcription of the AAV cap genes. The cap proteins then utilize the ITR sequences to package the rAAV genome into an rAAV viral particle. Therefore, the efficiency of packaging is determined, in part, by the availability of adequate amounts of the structural proteins, as well as the accessibility of any cis-acting packaging sequences required in the rAAV vector genome.

Retrovirus vectors are a common tool for gene delivery (Miller, Nature (1992) 357:455-460). The ability of retrovirus vectors to deliver an unrearranged, single copy gene into a broad range of rodent, primate and human somatic cells makes retroviral vectors well suited for transferring genes to a cell.

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus. A helper virus is not required for the production of the recombinant retrovirus if the sequences for encapsidation are provided by co-transfection with appropriate vectors.

The retroviral genome and the proviral DNA have three genes: the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vit vpr, tat, rev, vpu, nef, and vpx (in HIV-1, HIV-2 and/or SIV). Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all varion proteins.

Lentiviruses are complex retroviruses which, in addition to the common retroviral genes gag, pol and env, contain other genes with regulatory or structural function. The higher complexity enables the lentivirus to modulate the life cycle thereof, as in the course of latent infection. A typical lentivirus is the human immunodeficiency virus (HIV), the etiologic agent of AIDS. In vivo, HIV can infect terminally differentiated cells that rarely divide, such as lymphocytes and macrophages. In vitro, HIV can infect primary cultures of monocyte-derived macrophages (MDM) as well as HeLa-Cd4 or T lymphoid cells arrested in the cell cycle by treatment with aphidicolin or gamma irradiation. Infection of cells is dependent on the active nuclear import of HIV preintegration complexes through the nuclear pores of the target cells. That occurs by the interaction of multiple, partly redundant, molecular determinants in the complex with the nuclear import machinery of the target cell. Identified determinants include a functional nuclear localization signal (NLS) in the gag matrix (MA) protein, the karyophilic virion-associated protein, vpr, and a C-terminal phosphotyrosine residue in the gag MA protein. The use of retroviruses for gene therapy is described, for example, in U.S. Pat. Nos. 6,013,516; and 5,994,136, the disclosures of which are hereby incorporated herein by reference.

The inventors have discovered that intraventricular delivery of lysosomal hydrolase enzymes to patients who are deficient in the enzymes, leads to improved metabolic status of both the brain and the affected visceral (non-CNS) organs. This is particularly true when the delivery rate is slow, relative to a bolus delivery. One particularly useful enzyme for treating Niemann-Pick A, B, or D is acid sphingomyelinase (aSM), such as that shown in SEQ ID NO: 1.[1]

Although a particular amino acid sequence is shown in SEQ ID NO: 1, normal variants in the human population which retain activity can be used as well. Typically these normal variants differ by just one or two residues from the sequence shown in SEQ ID NO: 1. The variants to be used should be at least 95%, 96%, 97%, 98%, or 99% identical to SEQ ID NO: 1. Variants which are associated with disease or reduced activity should not be used. Typically the mature form of the enzyme will be delivered. This will begin with residue 47 as shown in SEQ ID NO: 1. Variants which are associated with disease are shown in FIG. 7.

Kits according to the present invention are assemblages of separate components. While they can be packaged in a single container, they can be subpackaged separately. Even a single container can be divided into compartments. Typically a set of instructions will accompany the kit and provide instructions for delivering the diagnostic, therapeutic, or anesthetic agents, such as lysosomal hydrolase enzymes, intraventricularly. The instructions may be in printed form, in electronic form, as an instructional video or DVD, on a compact disc, on a floppy disc, on the internet with an address provided in the package, or a combination of these means. Other components, such as diluents, buffers, solvents, tape, screws, and maintenance tools can be provided in addition to the agent, one or more cannulae or catheters, and/or a pump. Printed matter or other instructional materials may correlate volume of CSF, turn-over time of CSF, patient weight, patient age, delivery rate, delivery time, and/or other parameters. Pumps may be calibrated to deliver at specified rates based on CSF volume and/or turn-over time and/or patient age and/or patient weight.

The populations treated by the methods of the invention include, but are not limited to, patients having or at risk for developing a neurometabolic disorder, e.g., an LSD, such as diseases listed in Table 1, particularly, if such a disease affects the CNS and visceral organs. In an illustrative embodiment, the disease is type A Niemann-Pick disease. If genetic propensity for the disease has been determined, treatment may begin prenatally. Other diseases or conditions which may be treated include but are not limited to neurosurgical patients, stroke patients, Huntington's disease, epilepsy, Parkinson's disease, Lou Gehrig's disease, Alzheimer's disease.

An agent, such as a lysosomal hydrolase enzyme, can be incorporated into a pharmaceutical composition. The composition can be useful to diagnose, anesthetize, or treat, e.g., inhibit, attenuate, prevent, or ameliorate, a condition characterized by an insufficient level of a lysosomal hydrolase activity. The pharmaceutical composition can be administered to a subject suffering from a lysosomal hydrolase deficiency or someone who is at risk of developing said deficiency. The compositions should contain a an effective diagnostic, anesthetic, therapeutic or prophylactic amount of the agent, in a pharmaceutically-acceptable carrier. The pharmaceutical carrier can be any compatible, non-toxic substance suitable to deliver the polypeptides to the patient. Sterile water, alcohol, fats, and waxes may be used as the carrier. Pharmaceutically-acceptable adjuvants, buffering agents, dispersing agents, and the like, may also be incorporated into the pharmaceutical compositions. The carrier can be combined with the agent in any form suitable for administration by intraventricular injection or infusion (also possibly intravenous or intrathecal) or otherwise. Suitable carriers include, for example, physiological saline, bacteriostatic water, Cremophor EL™ (BASF, Parsippany, N.J.) or phosphate buffered saline (PBS), other saline solutions, dextrose solutions, glycerol solutions, water and oils emulsions such as those made with oils of petroleum, animal, vegetable, or synthetic origin (peanut oil, soybean oil, mineral oil, or sesame oil). An artificial CSF can be used as a carrier. The carrier will preferably be sterile and free of pyrogens. The concentration of the agent in the pharmaceutical composition can vary widely, i.e., from at least about 0.01% by weight, to 0.1% by weight, to about 1% weight, to as much as 20% by weight or more.

For intraventricular administration, the composition must be sterile and should be fluid. It must be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition.

Dosage of any agent, whether aSM or other lysosomal hydrolase enzyme, may vary somewhat from individual to individual, depending on the particular agent or enzyme and its specific in vivo activity, the route of administration, the medical condition, age, weight or sex of the patient, the patient's sensitivities to the aSM agent or components of vehicle, and other factors which the attending physician will be capable of readily taking into account. While dosages may vary depending on the disease and the patient, the enzyme is generally administered to the patient in amounts of from about 0.1 to about 1000 milligrams per 50 kg of patient per month, preferably from about 1 to about 500 milligrams per 50 kg of patient per month.

One way for delivering a slow infusion is to use a pump. Such pumps are commercially available, for example, from Alzet (Cupertino, Calif.) or Medtronic (Minneapolis, Minn.). The pump may be implantable or external. Another convenient way to administer the enzymes, is to use a cannula or a catheter. The cannula or catheter may be used for multiple administrations separated in time. Cannulae and catheters can be implanted stereotaxically. It is contemplated that multiple administrations will be used to treat the typical patient with a lysosomal storage disease. Catheters and pumps can be used separately or in combination. Catheters can be inserted surgically, as is known in the art. Kits can comprise an agent and a catheter and/or a pump. The pump may have settings suitable for delivery rates based on the volume of CSF in an individual.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Animal Model

ASMKO mice are an accepted model of types A and B Niemann-Pick disease (Horinouchi et al. (1995) Nat. Genetics, 10:288-293; Jin et al. (2002) J. Clin. Invest., 109:1183-1191; and Otterbach (1995) Cell, 81:1053-1061). Niemann-Pick disease (NPD) is classified as a lysosomal storage disease and is an inherited neurometabolic disorder characterized by a genetic deficiency in acid sphingomyelinase (ASM; sphingomyelin cholinephosphohydrolase, EC 3.1.3.12). The lack of functional ASM protein results in the accumulation of sphingomyelin substrate within the lysosomes of neurons and glia throughout the brain. This leads to the formation of large numbers of distended lysosomes in the perikaryon, which are a hallmark feature and the primary cellular phenotype of type A NPD. The presence of distended lysosomes correlates with the loss of normal cellular function and a progressive neurodegenerative course that leads to death of the affected individual in early childhood (The Metabolic and Molecular Bases of Inherited Diseases, eds. Scriver et al., McGraw-Hill, New York, 2001, pp. 3589-3610). Secondary cellular phenotypes (e.g., additional metabolic abnormalities) are also associated with this disease, notably the high level accumulation of cholesterol in the lysosomal compartment. Sphingomyelin has strong affinity for cholesterol, which results in the sequestering of large amounts of cholesterol in the lysosomes of ASMKO mice and human patients (Leventhal et al. (2001) J. Biol. Chem., 276:44976-44983; Slotte (1997) Subcell. Biochem., 28:277-293; and Viana et al. (1990) J. Med. Genet., 27:499-504.)

Example 2

Intraventricular Infusion of rhASM in the ASMKO Mouse II

Goal: To determine what effect intraventricular infusion of rhASM has on storage pathology (i.e., sphingomyelin and cholesterol storage) in the ASMKO mouse brain Methods: ASMKO mice were stereotaxically implanted with an indwelling guide cannula between 12 and 13 weeks of age. At 14 weeks of age mice were infused with 0.250 mg of hASM (n=5) over a 24 h period (~0.01 mg/h) for four straight days (1 mg total was administered) using an infusion probe (fits inside the guide cannula) which is connected to a pump. Lyophilized hASM was dissolved in artificial cerebral spinal fluid (aCSF) prior to infusion. Mice were sacrificed 3 days post infusion. At sacrifice mice were overdosed with euthasol (>150 mg/kg) and then perfused with PBS or 4% parformaldehyde. Brain, liver, lung and spleen were removed and analyzed for sphingomyelin (SPM) levels. Brain tissue was divided into 5 sections before SPM analysis (S1=front of brain, S5=back of the brain; see FIG. 1)

TABLE 2

| Group | Treatment | n |
|---|---|---|
| ASMKO | .250 mg/24 h (1 mg total) | 5 |
| ASMKO | None | 4 |
| WT | None | 4 |

Results summary: Intraventricular infusion of hASM at 0.250 mg/24 h for 4 continuous days (1 mg total) resulted in hASM staining and filipin (i.e., cholesterol storage) clearance throughout the ASMKO brain. Biochemical analysis showed that intraventricular infusion of hASM also led to a global reduction in SPM levels throughout the brain. SPM levels were reduced to that of wild type (WT) levels. A significant reduction in SPM was also observed in the liver and spleen (a downward trend was seen in the lung).

Example 3

Intraventricular Delivery of hASM in ASMKO Mice III

Goal: to determine lowest efficacious dose over a 6 h infusion period.

Methods: ASMKO mice were stereotaxically implanted with an indwelling guide cannula between 12 and 13 weeks of age. At 14 weeks of age mice were infused over a 6 period at one of the following doses of hASM: 10 mg/kg (0.250 mg; n=12), 3 mg/kg (0.075 mg; n=7), 1 mg/kg (0.025 mg; n=7), 0.3 mg/kg (0.0075 mg; n=7), or aCSF (artificial cerebral spinal fluid; n=7). Two mice from each dose level were perfused with 4% parformaldehyde immediately following the 6 h infusion to assess enzyme distribution in the brain (blood was also collected from these to determine serum hASM levels). The remaining mice from each group were sacrificed 1 week post infusion. Brain, liver, and lung tissue from these mice was analyzed for SPM levels as in study 05-0208.

TABLE 3

| Group | Treatment | n |
|---|---|---|
| ASMKO | 0.250 mg (10 mg/kg) | 12 |
| ASMKO | 0.075 mg (3 mg/kg) | 7 |
| ASMKO | 0.025 mg (1 mg/kg) | 7 |
| ASMKO | 0.0075 mg (.3 mg/kg) | 7 |
| ASMKO | aCSF | 7 |
| WT | None | 7 |

Results summary: Intraventricular hASM over a 6 h period led to a significant reduction in SPM levels throughout the brain regardless of does. Brains SPM levels in mice treated with doses >0.025 mg were reduced to WT levels. Visceral organ SPM levels were also significantly reduced (but not to WT levels) in a dose dependent manner. In support of this finding hASM protein was also detected in the serum of ASMKO mice infused with hASM protein. Histological analysis showed that hASM protein was widely distributed throughout the brain (from S1 to S5) after intraventricular administration of hASM.

Example 4

Intraventricular Infusion of rhASM in ASMKO Mice IV

Goal: To determine (1) the time it takes for SPM to reaccumulate within the brain (and spinal cord) after a 6 h infusion of hASM (dose=0.025 mg); (2) if there are sex differences in response to intraventricular hASM administration (pervious experiments demonstrate that there are sex differences in substrate accumulation in the liver, whether or not this occurs in the brain is unknown).

Methods: ASMKO mice were stereotaxically implanted with an indwelling guide cannula between 12 and 13 weeks of age. At 14 weeks of age mice were infused over a 6 period with 0.025 mg of hASM. After intraventricular delivery of hASM mice were sacrificed either at 1 week post infusion (n=7 males, 7 females), or at 2 weeks post infusion (n=7 males, 7 females) or at 3 weeks post infusion (n=7 males, 7 females). At sacrifice the brain, spinal cord, liver and lung were removed for SPM analysis.

| Group | Treatment | n | Sacrifice |
|---|---|---|---|
| male ASMKO | .025 mg | 7 | 1 week post infusion |
| Female ASMKO | .025 mg | 7 | 1 week post infusion |
| male ASMKO | .025 mg | 7 | 2 weeks post infusion |
| Female ASMKO | .025 mg | 7 | 2 weeks post infusion |
| male ASMKO | .025 mg | 7 | 3 weeks post infusion |
| Female ASMKO | .025 mg | 7 | 3 weeks post infusion |
| male ASMKO | aCSF | 7 | 1 week post infusion |
| Female ASMKO | aCSF | 7 | 1 week post infusion |
| male WT | None | 7 | 1 week post infusion |
| Female WT | None | 7 | 1 week post infusion |

Tissue samples are prepared for SPM analysis.

Example 5

Effect of Intraventricular Infusion of rhASM on Cognitive Function in ASMKO Mice Goal: to determine if intraventricular infusion of rhASM alleviates diseased induced cognitive deficits in ASMKO mice Methods: ASMKO mice will be stereotaxically implanted with an indwelling guide cannula between 9 and 10 weeks of age. At 13 weeks of age mice will be infused over a 6 period with 0.025 mg of hASM. At 14 and 16 weeks of age mice will undergo cognitive testing using the Barnes maze.

Example 6 hASM Protein Distribution within the ASMKO CNS after Intraventricular Infusion

Goal: to determine the distribution of hASM protein (as function of time) within the brain and spinal cord of ASMKO mice after intraventricular infusion Methods: ASMKO mice will be stereotaxically implanted with an indwelling guide cannula between 12 and 13 weeks of age. At 14 weeks of age mice will be infused over a 6 period with 0.025 mg of hASM. Following infusion procedure mice will either be sacrificed immediately or 1 week or 2 weeks or 3 weeks later.

REFERENCES

The disclosure of each reference cited is expressly incorporated herein.
1) Belichenko P V, Dickson P I, Passage M, Jungles S, Mobley W C, Kakkis E D. Penetration, diffusion, and uptake of recombinant human alpha-1-iduronidase after intraventricular injection into the rat brain. Mol Genet Metab. 2005; 86(1-2):141-9.
2) Kakkis E, McEntee M, Vogler C, Le S, Levy B, Belichenko P, Mobley W, Dickson P, Hanson S, Passage M. Intrathecal enzyme replacement therapy reduces lysosomal storage in the brain and meninges of the canine model of MPS I. Mol Genet Metab. 2004; 83(1-2):163-74.
3) Bembi B, Ciana G, Zanatta M, et al. Cerebrospinal-fluid infusion of alglucerase in the treatment for acute neuronopathic Gaucher's disease. Pediatr Res 1995; 38:A425.
4) Lonser R R, Walbridge S, Murray G J, Aizenberg M R, Vortmeyer A O, Aerts J M, Brady R O, Oldfield E H. Convection perfusion of glucocerebrosidase for neuronopathic Gaucher's disease. Ann Neurol. 2005 April; 57(4): 542-8.

We claim:
1. A method for delivering an agent to a patient's brain, the method comprising:
estimating turn-over time of cerebrospinal fluid of the patient;
selecting a rate and a total delivery time for an agent via a lateral ventricle of the brain based on the turn-over time;
setting a pump to deliver the agent at said selected rate for said total delivery time, wherein the rate delivers a single dose of the agent for a time greater than or equal to 50% of the turn-over time,
wherein the agent is an enzyme that is deficient in a lysosomal storage disease.
2. A method for delivering an agent to a patient's brain, the method comprising:
estimating turn-over time of cerebrospinal fluid of the patient;
selecting a rate and a total delivery time for an agent via a lateral ventricle of the brain based on the turn-over time; and
delivering the agent to the patient at said selected rate for said total delivery time, wherein the rate delivers a single dose of the agent for a time greater than or equal to 50% of the turn-over time,
wherein the agent is an enzyme that is deficient in a lysosomal storage disease.
3. The method of claim 1, wherein the rate delivers a single dose of the agent for a time greater than or equal to 100% of the estimated turn-over time.
4. The method of claim 2, wherein the rate delivers a single dose of the agent for a time greater than or equal to 100% of the estimated turn-over time.
5. The method of claim 1, wherein the rate delivers a single dose of the agent for a time greater than or equal to 150% of the estimated turn-over time.
6. The method of claim 2, wherein the rate delivers a single dose of the agent for a time greater than or equal to 150% of the estimated turn-over time.
7. The method of claim 1, wherein the agent accesses the serum.
8. The method of claim 1, wherein the agent is sphingomyelinase.
9. The method of claim 1, wherein the lysosomal storage disease is Niemann-Pick B disease.
10. The method of claim 2, wherein the agent is delivered using an implantable pump.
11. The method of claim 2, wherein the agent accesses the serum.
12. The method of claim 2, wherein the agent is sphingomyelinase.
13. The method of claim 2, wherein the lysosomal storage disease is Niemann-Pick B disease.
14. The method of claim 9, wherein the agent is acid sphingomyelinase.
15. The method of claim 13, wherein the agent is acid sphingomyelinase.

* * * * *